(12) United States Patent
Van der Westhuizen et al.

(10) Patent No.: US 9,181,293 B2
(45) Date of Patent: Nov. 10, 2015

(54) METHOD FOR THE SYNTHESIS OF ASPALATHIN AND ANALOGUES THEREOF

(75) Inventors: Jan Hendrik Van der Westhuizen, Bayswater (ZA); Daneel Ferreira, Oxford, MS (US); Elizabeth Joubert, Emerald View (ZA); Sussana Lucia Bonnet, Bloemfontein (ZA)

(73) Assignee: South African Medical Research Council, Parow (ZA)

( * ) Notice: Subject to any disclaimer, the term of this patent is extended or adjusted under 35 U.S.C. 154(b) by 648 days.

(21) Appl. No.: 13/511,712

(22) PCT Filed: Nov. 24, 2010

(86) PCT No.: PCT/IB2010/055398
§ 371 (c)(1),
(2), (4) Date: Oct. 2, 2012

(87) PCT Pub. No.: WO2011/064726
PCT Pub. Date: Jun. 3, 2011

(65) Prior Publication Data
US 2013/0018182 A1    Jan. 17, 2013

(30) Foreign Application Priority Data
Nov. 24, 2009    (ZA) .................................. 2009/08308

(51) Int. Cl.
*C07H 1/00*    (2006.01)
*C07H 15/203*    (2006.01)

(52) U.S. Cl.
CPC .................................... *C07H 15/203* (2013.01)

(58) Field of Classification Search
CPC ........... C07H 7/04; C07H 1/00; C07H 15/203
USPC ............................................. 536/124; 514/23
See application file for complete search history.

(56) References Cited

FOREIGN PATENT DOCUMENTS

JP    2007-197409 A    8/2007

OTHER PUBLICATIONS

Kumazawa et al. (Carbohydrate Research 334 (2001) 183-193).*
S. Sato et al., Studies on the synthesis of safflomin-A, a yellow pigment in safflower petals: Oxidation of 3-C-beta.-D-glucopyranosyl-5-methylphloroacetophenone, Carbohydrate Research, vol. 340, 2005, pp. 389-393.
S. Sato et al., Scandium cation-exchanged montmorillortite catalyzed direct C-glycosylation of a 1,3-diketone, dimedone, with unprotected sugars in aqueous solution, Carbohydrate Research, vol. 342, 2007, pp. 913-918.
S. Sato et al, Total synthesis of three naturally occurring 6,8-di-C-glycosylflavonoids: phloretin, naringenin, and apigenin bis-C-beta-D-glucosides, Carbohydrate Research, vol. 341, 2006, pp. 964-970.
Office Action issued Dec. 1, 2014 in corresponding Japanese patent application No. 2012-540528 with English translation (11 pages).

* cited by examiner

*Primary Examiner* — Shaojia Anna Jiang
*Assistant Examiner* — Michael C Henry
(74) *Attorney, Agent, or Firm* — Raymond R. Ferrera; Adams and Reese LLP

(57) ABSTRACT

A method of synthesising Aspalathin and its analogues or derivatives is disclosed. The method comprises synthesising a compound of formula 1 or its analogues or derivatives:

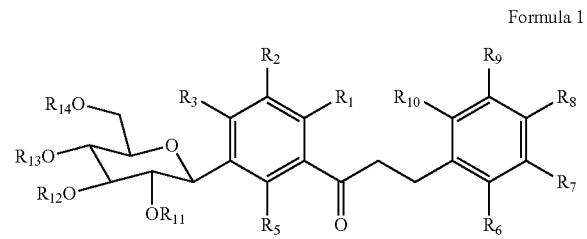

Formula 1 wherein
each of $R_1$, $R_2$, $R_3$, $R_4$, $R_5$, $R_6$, $R_7$, $R_8$, $R_9$ and $R_{10}$ is independently selected from the group consisting of —H, —OH, hydrocarbyl groups, saccharide moieties and —$OR_{15}$;
$R_{15}$ is selected from the group consisting of hydrogen, a hydrocarbyl group (e.g. methoxy or ethoxy), an acyl group and a benzyl group; and
$R_{11}$, $R_{12}$, $R_{13}$ and $R_{14}$ are independently selected from the group consisting of —H, hydrocarbyl groups, saccharide moieties, an acyl group and a benzyl group. The method comprises the step of coupling a sugar to a dihydrochalcone, chalcone or flavanone, or coupling the sugar to an intermediate for producing a dihydrochalcone, chalcone or flavanone followed by coupling of the sugar-intermediate adduct to a further intermediate for producing a dihydrochalcone, chalcone or flavanone, and transforming the product thereof into a compound of formula 1 or an analogue or derivative thereof.

5 Claims, No Drawings

METHOD FOR THE SYNTHESIS OF ASPALATHIN AND ANALOGUES THEREOF

CROSS REFERENCE TO RELATED APPLICATIONS

This application is the National Stage of International Application No. PCT/IB2010/055398, filed Nov. 24, 2010.

BACKGROUND OF THE INVENTION

This invention relates to a novel process for the synthesis of aspalathin (3-(3,4-dihydroxyphenyl)-1-(3-beta-D-glucopyranosyl-2,4,6-trihydroxyphenyl)-1-propanone (Formula A) and analogues thereof.

Aspalathin and its analogues occur in nature in plants. Significant biological activities have been attributed to this class of compounds.

Aspalathin and its analogues consist of three building blocks:
 a sugar (saccharide) moiety, typically D-glucose;
 a mono- or polyhydroxylated aromatic ring, typically phloroglucinol (ring B in formula A); and
 a 3-phenyl propanoid moiety, typically 3-(3',4'-hydroxyphenyl)-1-propanone (ring A in formula A).

The sugar moiety is linked at its anomeric (C-1) position (C-1" in formula A) to the polyhydroxylated aromatic ring via a carbon-carbon bond. Aspalathin and analogues are thus C-glycosides. The anomeric carbon in aspalathin is in the β-configuration but in analogues it can be in the β- or α-configuration. In analogues of aspalathin the sugar moiety can be any sugar, including monosaccharides, disaccharides and polysaccharides (examples include the D- and L-forms of ribose, arabinose, galactose, fructose, sucrose etc.). A sugar is defined as a polyhydroxylated aldehyde or ketone. Sugars typically have five or six carbon atoms and typically, but not always, occur as a cyclic acetal in aspalathin and analogues. The sugar moiety is normally in the free hydroxy form but may be fully or selectively derivatised. For example, it may occur as methyl or benzyl ethers or as acetates. The sugar moiety is typically an underivatised D-glucose acetal in the β-configuration, as in formula A.

The propanoid moiety is linked to the polyhydroxylated aromatic ring via a carbon-carbon bond between the aromatic ring and the carbonyl carbon on the propanoid moiety. The moiety without the sugar molecule is thus a dihydrochalcone. The propanoid moiety has a carbonyl group and can also have a double bond conjugated with the carbonyl group. In this case, the moiety of aspalathin and analogues without the sugar is a chalcone. The propanoid moiety typically has a carbonyl in the 1-position and occurs without a double bond, and is thus part of a dihydrochalcone moiety, as in formula A.

The phenyl group (ring A in formula A) on the 3-position of the propanoid moiety can have zero, one, two, three, four or five hydroxy groups on any of the available aromatic carbons. For example, the analogue with only one hydroxy can have this hydroxyl group in the 2, 3 or 4 position and the analogue with two hydroxyl groups has these typically in the 3,4-position as in formula A, but can also have these in the 2,3-position, 2,5-position, 3,5-position or 2,4-position. The analogue with three hydroxyl groups has these typically in the 3,4,5-position. The phenyl group of the propanoid moiety with one or more hydroxy groups is normally in the free hydroxy form but may be fully or selectively derivatised. For example, it may occur as methyl or benzyl ethers or as acetates.

The mono or polyhydroxylated aromatic ring (in the 1-position of the propanoid moiety) (ring B in formula A) acts as a linkage between the sugar moiety and the propanoid moiety. It can have one (in which case it is phenol), two (in which case it can be resorcinol), three (in which case it can be phloroglucinol or pyragallol) or four hydroxy groups. These hydroxy groups may be fully or selectively derivatised: for example, they may be methyl or benzyl ethers or acetates. They are typically an underivatised free phenolic phloroglucinol moiety, as in formula A.

Formula A

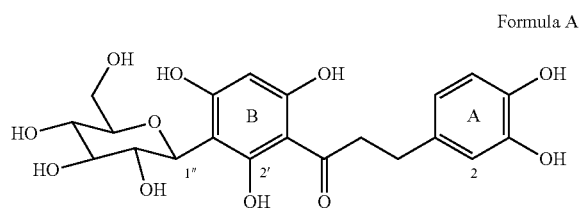

Aspalathin is usually extracted from *Aspalathus linearis* (rooibos plant) and there are no known references which describes the synthesis of this compound in yields of more than 2% or less than eight steps (Yepremyan, *Organic Letters*, 2010, 1580-1583).

There is therefore a need for a method of synthesising aspalathin and its analogues in commercially viable quantities in a few steps from easily available starting materials.

SUMMARY OF THE INVENTION

According to a first embodiment of the invention, there is provided a method for synthesising a compound of formula 1 or an analogue or derivative thereof:

Formula 1

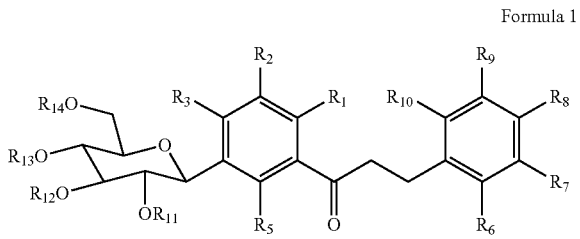

wherein
 each of $R_1$, $R_2$, $R_3$, $R_5$, $R_6$, $R_7$, $R_8$, $R_9$ and $R_{10}$ is independently selected from the group consisting of —H, —OH, hydrocarbyl groups, saccharide moieties and —$OR_{15}$;
 $R_{15}$ is selected from the group consisting of hydrogen, a hydrocarbyl group (e.g. methyl or ethyl), an acyl group and a benzyl group; and
 $R_{11}$, $R_{12}$, $R_{13}$ and $R_{14}$ are independently selected from the group consisting of —H, hydrocarbyl groups, saccharide moieties, an acyl group and a benzyl group;
 and wherein the method comprises the step of coupling an unprotected or protected sugar to an unprotected or protected dihydrochalcone or chalcone, or coupling the sugar to an intermediate for producing a dihydrochalcone or chalcone followed by coupling of the sugar-intermediate adduct to a further intermediate for producing a dihydrochalcone or chalcone and transforming the product thereof into a compound of formula 1 or an analogue or derivative thereof.

The analogue may be a compound of formula 2:

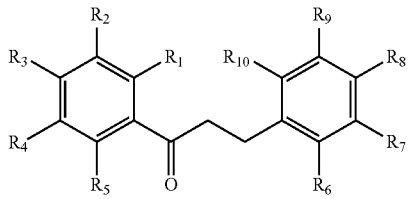

Formula 2

In the analogue of formula 2, at least one of $R_1$, $R_2$, $R_3$, $R_4$ or $R_5$ may be a monosaccharide, disaccharide or oligomer of a saccharide. The monosaccharide, disaccharide or oligomer of the saccharide may be attached at the anomeric carbon (C-1 of the saccharide) to the aromatic ring via a carbon-carbon bond.

The analogue may also contain a double bond in the propanoid unit (formula 3):

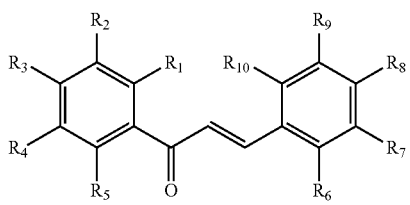

Formula 3

$R_1$, $R_2$, $R_3$, $R_4$ or $R_5$ being as defined for the analogue of formula 2.

Analogues of formula 1 may be peracetate, permethyl, perbenzyl, monohydroxy or perhydroxy forms of aspalathin or various combinations of hydroxyl and acetate, methyl or benzyl groups. The perbenzyl, permethyl or peracetate forms of formula 1 may be converted to a compound of formula A by hydrogenation and/or treatment with a weak acid or base or BBr$_3$:

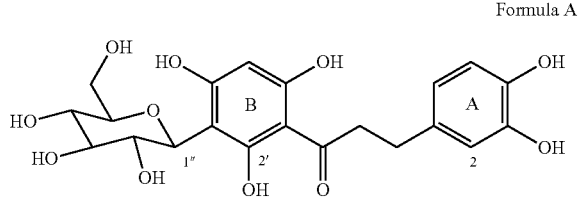

Formula A

The sugar may be any sugar, including monosaccharides, disaccharides and polysaccharides (examples include the D- and L-forms of ribose, arabinose, galactose, fructose, sucrose and so forth). The sugar moiety may be in the free hydroxy form but may also be fully or selectively derivatised. For example, it may occur as a methyl or benzyl ether or as an acetate. The sugar moiety is typically an underivatised D-glucose acetal in the β-configuration, as in formula A.

The chalcone may be a compound of formula 4:

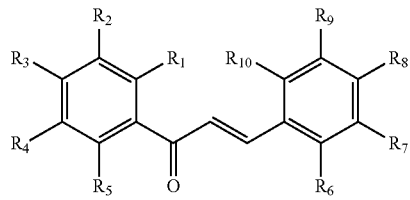

Formula 4 wherein
each of $R_1$, $R_2$, $R_3$, $R_4$, $R_5$, $R_6$, $R_7$, $R_8$, $R_9$ and $R_{10}$ is independently selected from the group consisting of —H, —OH, hydrocarbyl groups, saccharide moieties and —OR$_{15}$, and at least one of $R_1$, $R_2$, $R_3$, $R_4$, and $R_5$ is hydrogen (the hydrogen is replaced by the sugar moiety during the coupling reaction); and
$R_{15}$ is selected from the group consisting of hydrogen, a hydrocarbyl group (e.g. methyl or ethyl), an acyl group and a benzyl group.

The dihydrochalcone may be a compound of formula 5:

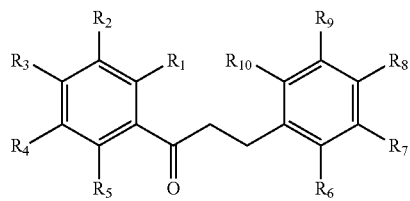

Formula 5 wherein
each of $R_1$, $R_2$, $R_3$, $R_4$, $R_5$, $R_6$, $R_7$, $R_8$, $R_9$ and $R_{10}$ is independently selected from the group consisting of —H, —OH, hydrocarbyl groups, saccharide moieties and —OR$_{15}$, and at least one of $R_1$, $R_2$, $R_3$, $R_4$, and $R_5$ is hydrogen (the hydrogen is replaced by the sugar moiety during the coupling reaction); and
$R_{15}$ is selected from the group consisting of hydrogen, a hydrocarbyl group (e.g. methyl or ethyl), an acyl group and a benzyl group.

The analogues may also be in the flavanone form of formula 6:

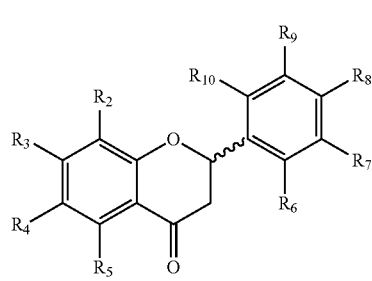

Formula 6 wherein
each of $R_2$, $R_3$, $R_4$, $R_5$, $R_6$, $R_7$, $R_8$, $R_9$ and $R_{10}$ is independently selected from the group consisting of —H, —OH, hydrocarbyl groups, saccharide moieties and —OR$_{15}$, and at least one of $R_1$, $R_2$, $R_3$, $R_4$, and $R_5$ is hydrogen (the hydrogen is replaced by the sugar moiety during the coupling reaction); and
$R_{15}$ is selected from the group consisting of a hydrogen, a hydrocarbyl group (e.g. methyl or ethyl), an acyl group and a benzyl group.

One or more hydroxy groups of the sugar may be protected prior to being coupled, typically as a benzyl, methyl, methoxymethyl ethers or acetate.

One or more hydroxy groups of the chalcone, dihydrochalcone, flavanone, polyhydroxylated aromatic ring, 3-phenyl propanoid, polyhydroxyphenol, polyhydroxybenzaldehyde or polyhydroxyacetophenone may be protected prior to being coupled, typically as a benzyl, methyl or methoxymethyl ether or acetates.

The protecting groups may be removed after the synthesis of aspalathin or its analogues.

The C-1 hydroxy group of the sugar may be replaced with another substituent, such as a trichloroacetimidate, trifluoroacetimidate, acetate, trifluoroacetate, a halide or a sulfur- or selenium-containing leaving group that reacts with a Lewis acid to increase the electrophilicity of the anomeric (C-1) carbon. This carbon (C-1) may also be activated by an epoxide between C-1 and C-2 (a 1,2-anhydrosugar). $ZnCl_2$ is typically used to interact with the epoxide ring and increase the electrophilicity of the C-1 carbon.

DETAILED DESCRIPTION OF THE INVENTION

A method for the synthesis of aspalathin and analogues is described herein. As described above, aspalathin and its analogues consist of a sugar moiety (typically D-glucose), a mono or polyhydroxylated aromatic ring (typically phloroglucinol) and a 3-phenyl propanoid moiety (typically 3-(3', 4'-hydroxyphenyl)-1-propanone).

A sugar is defined as a polyhydroxylated aldehyde or ketone. Sugars typically have five or six carbon atoms and typically, but not always, occur as a cyclic acetal in aspalathin and analogues.

Aspalathin and its analogues can be synthesised according to the invention by the step of coupling a sugar to a dihydrochalcone, chalcone or flavanone, or coupling the sugar to an intermediate for producing a dihydrochalcone, chalcone or flavanone followed by coupling of the sugar-intermediate adduct to a further intermediate for producing a dihydrochalcone, chalcone or flavanone, and transforming the product thereof into a compound of formula 1 or an analogue thereof.

In the case where a chalcone is the intermediate, the double bond of the chalcone may need to be reduced.

Enhanced electrophilicity at the anomeric (C-1) carbon of the sugar may be required to couple the sugar or saccharide via a carbon-carbon bond to the mono or polyhydroxylated aromatic ring (via Lewis acid or other catalytic activation methods). This can be achieved by substituting the hydroxy group at C-1 (the anomeric carbon) of the sugar molecule with other substituents, including a trifluoroacetimidate (formula a), a trichloroacetimidate (formula b), halides (e.g. using the Koenig-Knorr reaction) (formula c), and selenium or sulfur containing leaving groups (formula d). These substitution reactions make the anomeric OH a better leaving group. The electrophilicity of the anomeric carbon can also be enhanced by reacting the anomeric OH with trifluoroacetic anhydride to obtain a trifluoroacetate (formula e). The trifluoroacetate is not isolated and substitution of the trifluoroacetate with the aromatic ring is catalysed in situ by Lewis acids such as $BF_3$.

Enhanced electrophilicity at the anomeric carbon can also be achieved by using a 1,2 anhydrosugar (formula where the C-1 carbon is part of an epoxide moiety. The epoxide moiety between C-1 and C-2 of the sugar enhances the electrophilicity of the C-1 position. The 1,2 anhydro sugar is usually obtained via epoxidation of a glycal. This enhanced electrophilicity at the C-1 position allows attack by nucleophiles to generate C-glycosides. The other hydroxy groups on the sugar (excluding the C-1 hydroxy group) may need to be protected, typically as benzyl ethers or acetates. Protection of these groups may be to protect them from attack by nucleophiles, elimination, oxidation and the like.

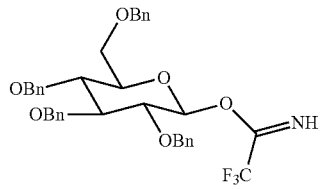

Formula a

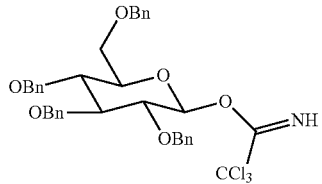

Formula b

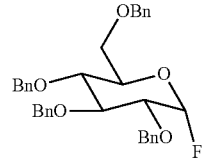

Formula c

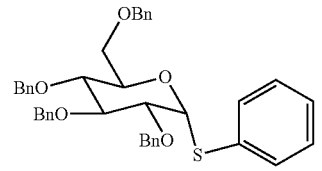

Formula d

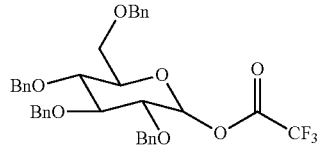

Formula e

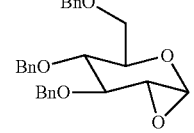

Formula f

A bulky protecting group on C-2 (e.g. a benzyl group) encourages formation of β-C-glucosides. Neighbouring group participation by acetate on C-2 usually allows exclusive (stereospecific) formation of the glucoside in the β-configuration. In the case of the glycal, the epoxide is formed trans to a bulky protecting group (e.g. a benzyl group) on C-3. Coupling of a nucleophile on C-1 is usually accompanied by opening of the epoxide ring and inversion of configuration at C-1. The configuration on C-3 may thus determine the α- or β-configuration of the C-glycoside. The glycal equivalent of glucose (formula g) will give a C-1 α-epoxide (formula h) and finally a β-glycoside.

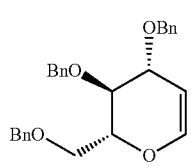

Formula g

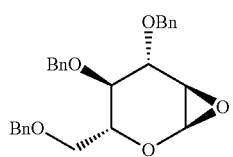

A C-1 activated sugar (e.g. formulas a to f) can be coupled to an aromatic ring (polyhydroxyphenol or polyhydroxyac-etophenone, protected or unprotected). In terms of the present invention, a quantitative conversion of formula i and formula j to formula k with trifluoroacetic anhydride (TFAA) (Scheme 1) is provided.

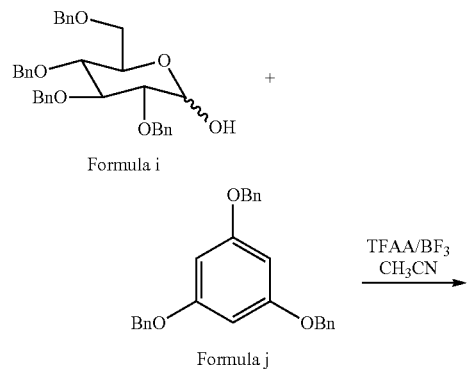

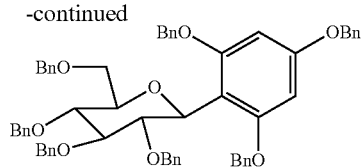

Formula k

A 3-phenylpropanoid unit can be coupled to a mono or polyhydroxyaromatic ring, typically via a chalcone (Formula n) (coupling of an acetophenone (Formula 1) to a benzaldehyde (formula m), followed by selective reduction of the alkene double bond with hydrogen over a catalyst (e.g. palladium on carbon) to obtain the required dihydrochalcone (Formula o) (Scheme 2).

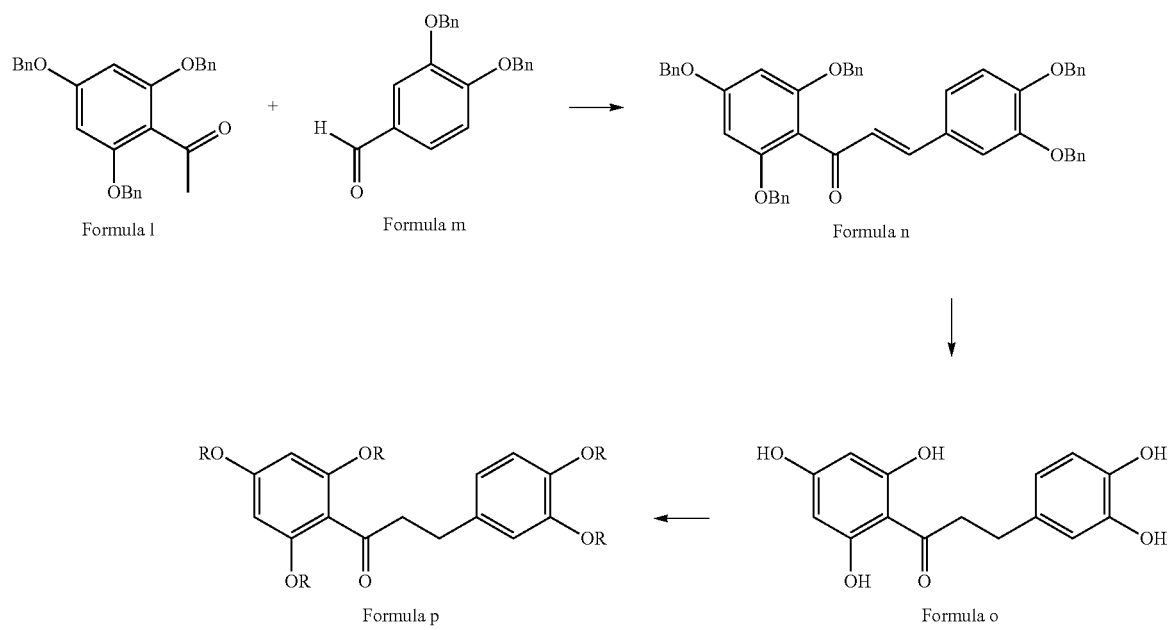

Efforts to add a sugar molecule to a protected dihydrochalcone (Formula p) (R=methoxy, benzyl etc.), proved extremely difficult. Without wishing to be bound by theory, it was postulated that the carbonyl group withdraws electrons from the aromatic ring and reduces its nucleophilicity towards the anomeric (C-1) carbon of the sugar. It was believed that by using free phenolic aromatic rings, the electron donating properties of the aromatic OH groups would counter the electron withdrawing properties of the carbonyl group to restore the nucleophilicity of the aromatic ring towards the C-1 sugar carbon. Accordingly, coupling of the free phenolic dihydrochalcone (o) with water tolerant Lewis acid (e.g. ScOTf) yielded aspalathin (Scheme 3).

Scheme 3.

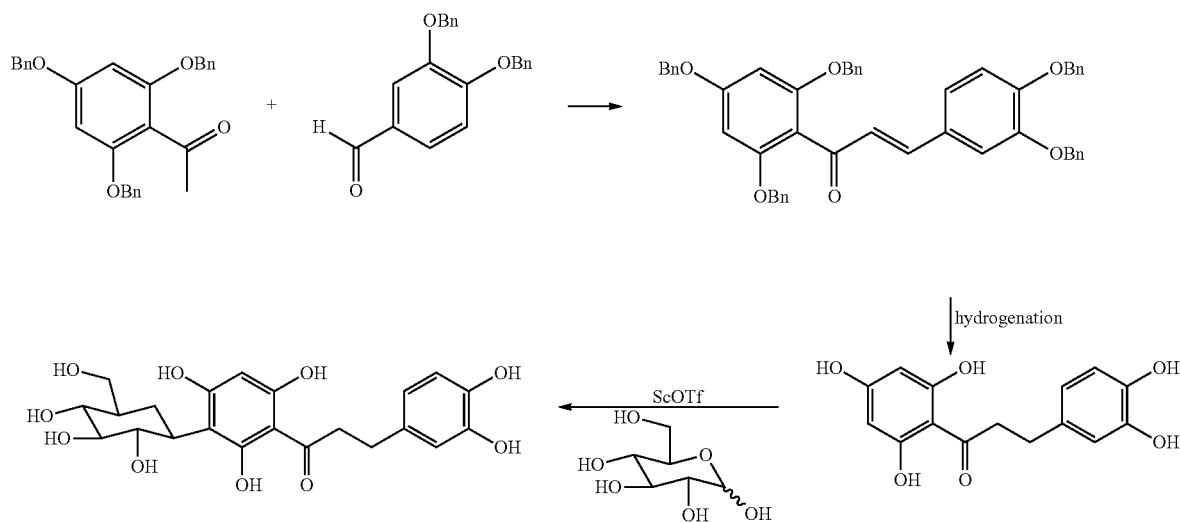

An alternative approach is to remove the carbonyl from the protected dihydrochalcone via reduction with hydrogen under more drastic conditions (palladium on carbon at 15 psi pressure or $NaBH_4$) to obtain formula q. The product (q) is coupled to a protected sugar (formula b) to yield formula r that can be transformed to aspalathin via benzylic oxidation and deprotection (Scheme 4).

Scheme 4.

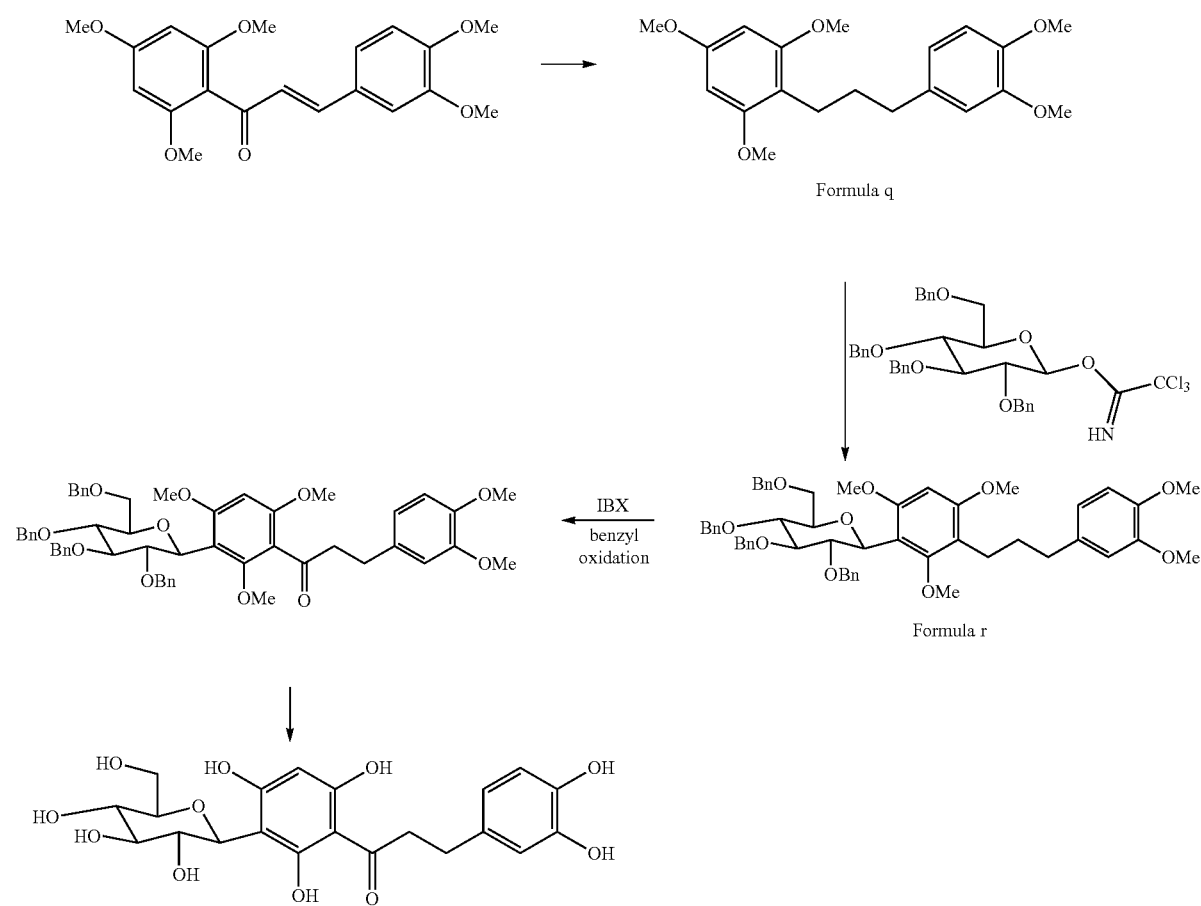

Accordingly, in some embodiments of the invention, an aromatic ring-propanoid moiety is constructed first, via reduction of a chalcone. The chalcone is constructed from a suitably substituted and protected phloroacetophenone and a benzaldehyde as starting materials. The nucleophilicity of the aromatic A-ring is activated by either: (a) using unprotected OH groups on the A-ring (scheme 3) or (b) removing the carbonyl oxygen completely from the dihydrochalcone (to be reintroduced after coupling) (scheme 4). The OH groups in (a) are electron donating and counter the electron withdrawing effects of the carbonyl group. Water resistant Lewis acid such ScOTf and InCl$_3$ is used.

In some embodiments of the invention, the sugar is coupled first to the aromatic A-ring to obtain the sugar aromatic ring adduct. This product is then attached to the propanoid moiety, either directly to a 3-phenylpropanoic acid derivative or via acylation to obtain a sugar-acetophenone intermediate (scheme 5). The intermediate is then reacted with a suitably protected or substituted benzaldehyde to yield a protected chalcone, which is reduced (hydrogenation of the alkene double bond) and deprotected to yield aspalathin or derivatives.

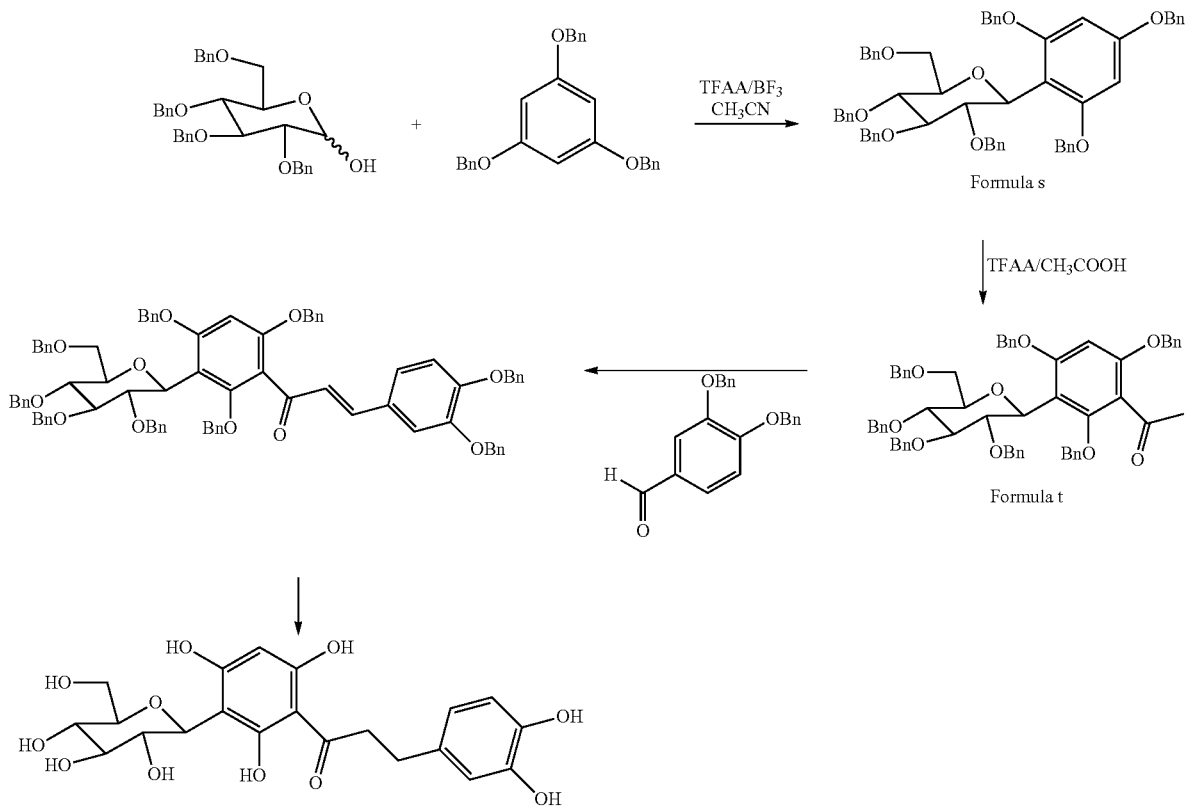

Scheme 5.

In some embodiments of the invention, acetic acid is replaced by a protected dihydrocaffeic acid (Formula tt) in the TFAA catalysed reaction to yield protected aspalathin directly (Scheme 6).

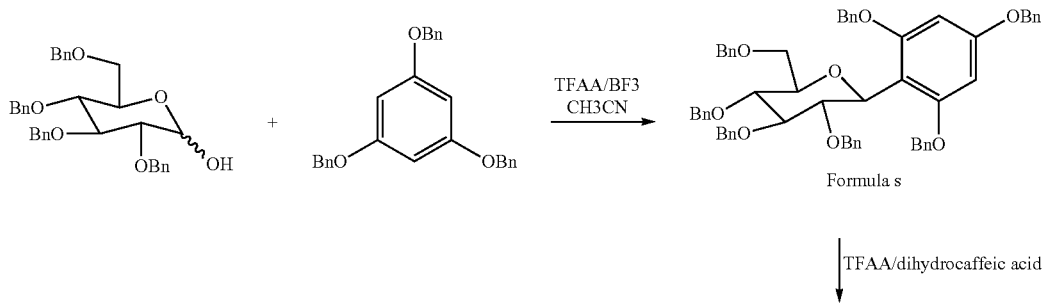

Scheme 6.

-continued

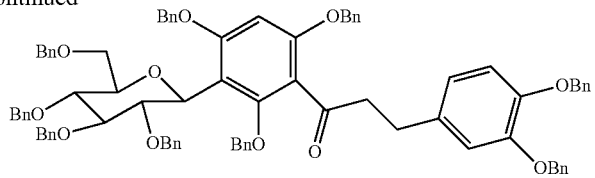

Efforts to add a propanoid moiety or an acyl group to the sugar-aromatic ring adduct (formula s) also proved difficult. Without wishing to be bound by theory, it is believed this is due to the Lewis acid removing or destroying the benzyl protecting groups. This problem was addressed by using trifluoroacetic acid anhydride (TFAA) in acetic acid. Reaction of the sugar-phloroglucinol adduct (Formula s) with TFAA in acetic acid yielded the acetophenone (Formula t) which could be transformed to aspalathin via chalcone formation and reduction of the alkene double bond and removal of the benzylprotecting groups. Replacement of acetic acid with protected dihydrocaffeic acid (Formula tt) in the TFAA catalysed reaction yielded protected aspalathin directly. The advantage of TFAA is that the benzyl protecting groups are not destroyed as is the case with Lewis acids.

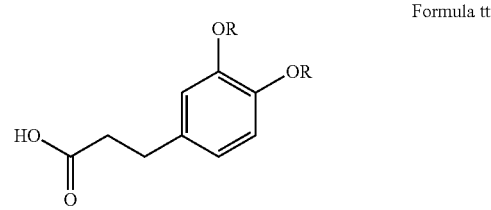

Formula tt

In some embodiments of the invention, an unprotected sugar is coupled to a free phenolic acetophenone (unprotected OH groups) according to the method described by Sato and co-workers (Carbohydrate Research, 2004, 2611-2614). This product is then transformed to a chalcone and the chalcone is reduced to aspalathin or analogues, depending on the substitution pattern on the starting material. An important aspect of these embodiments is the protection of the sugar-acetophenone coupled product, as unprotected (free phenolic acetophenone) is not reactive in chalcone formation, and the selective hydrogenation of the chalcone to aspalathin or analogues thereof.

Scheme 7.

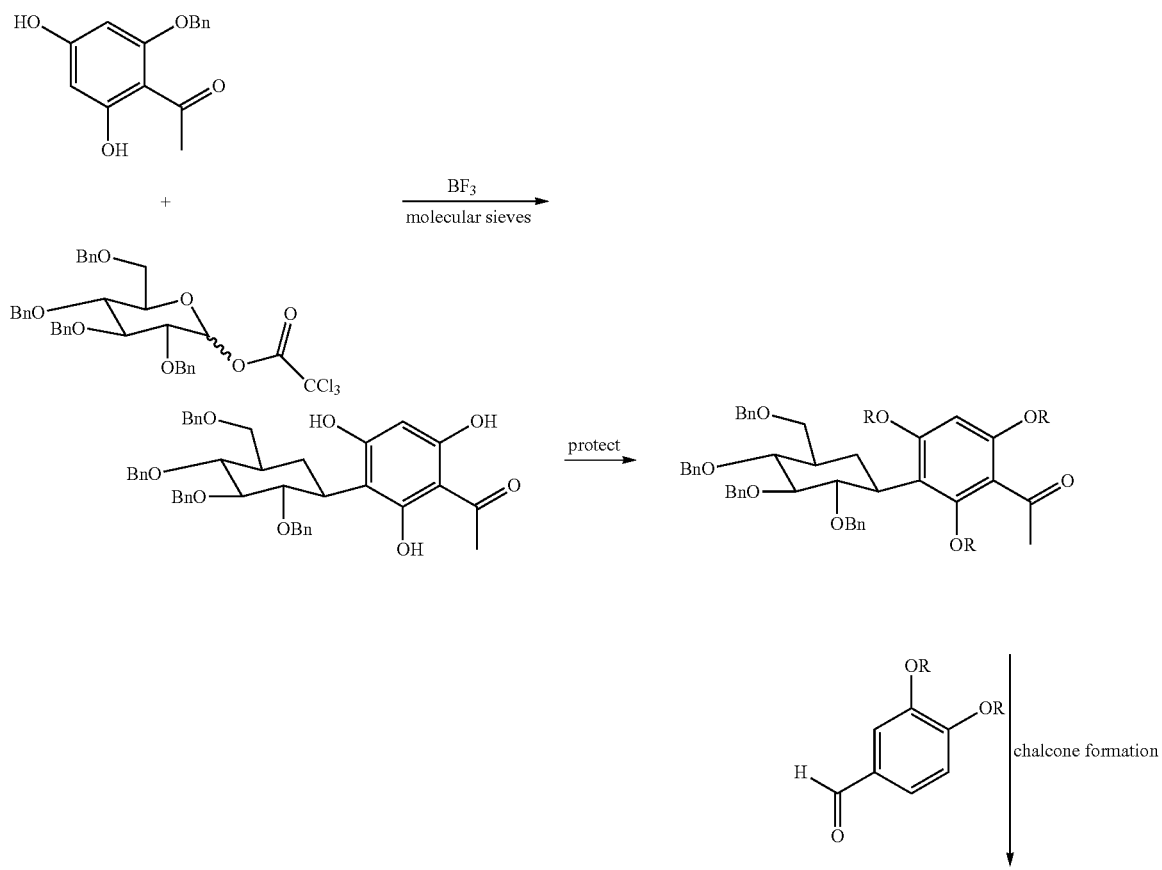

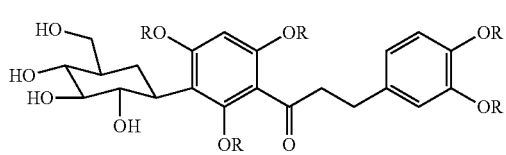
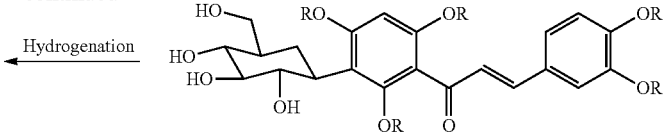

-continued

Hydrogenation

Deprotect

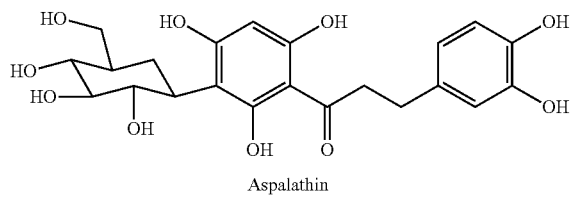

Aspalathin

The sugar-phloroacetophenone intermediate can be prepared by reacting a protected sugar imidate (e.g. Formula b) with free phenolic phloroacetophenone and coupling it to 3,4-di-O-benzylbenzaldehyde. Importantly, the free OH groups on the phloroacetophenone must be protected with benzyl, methoxymethyl or methoxy protecting groups as chalcone formation does not take place from unprotected phloroacetophenone (Scheme 7). It has also been possible to synthesise aspalathin via preparing by benzylating an intermediate prepared according to the method published by Sato (*Carbohydrate Research*, 2004, 2611-2614).

In some embodiments of the invention, a chalcone is formed according to the method used by Kumazawa and co-workers (*Bull. Chem. Soc. Jpn.*, 1995, 1379-1384) that relies on a acetophenone with one free OH on the aromatic A-ring. The unprotected OH reacts to form an O-glycoside. This commonly rearranges spontaneously to the C-glycoside. If not, the O-glycoside is transformed via heating, Lewis acid catalysis or photochemistry to the desired C-glycoside. The chalcone is then selectively reduced to aspalathin or its analogues (scheme 8).

Scheme 8.

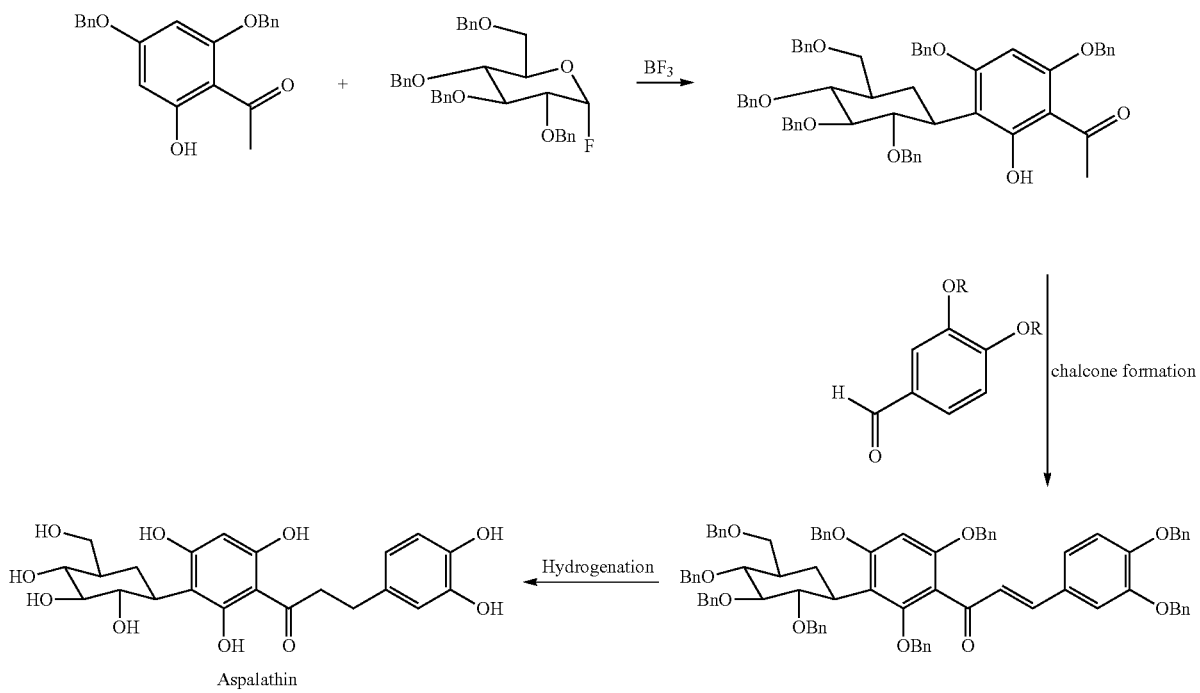

Aspalathin

In alternative embodiments, the fluorinated sugar is coupled to a flavone or flavanone (and not to an acetophenone) with a free phenolic OH on the A-ring and the coupled product transformed directly or indirectly (via a chalcone) to aspalathin or its analogues (scheme 9).

Scheme 9.

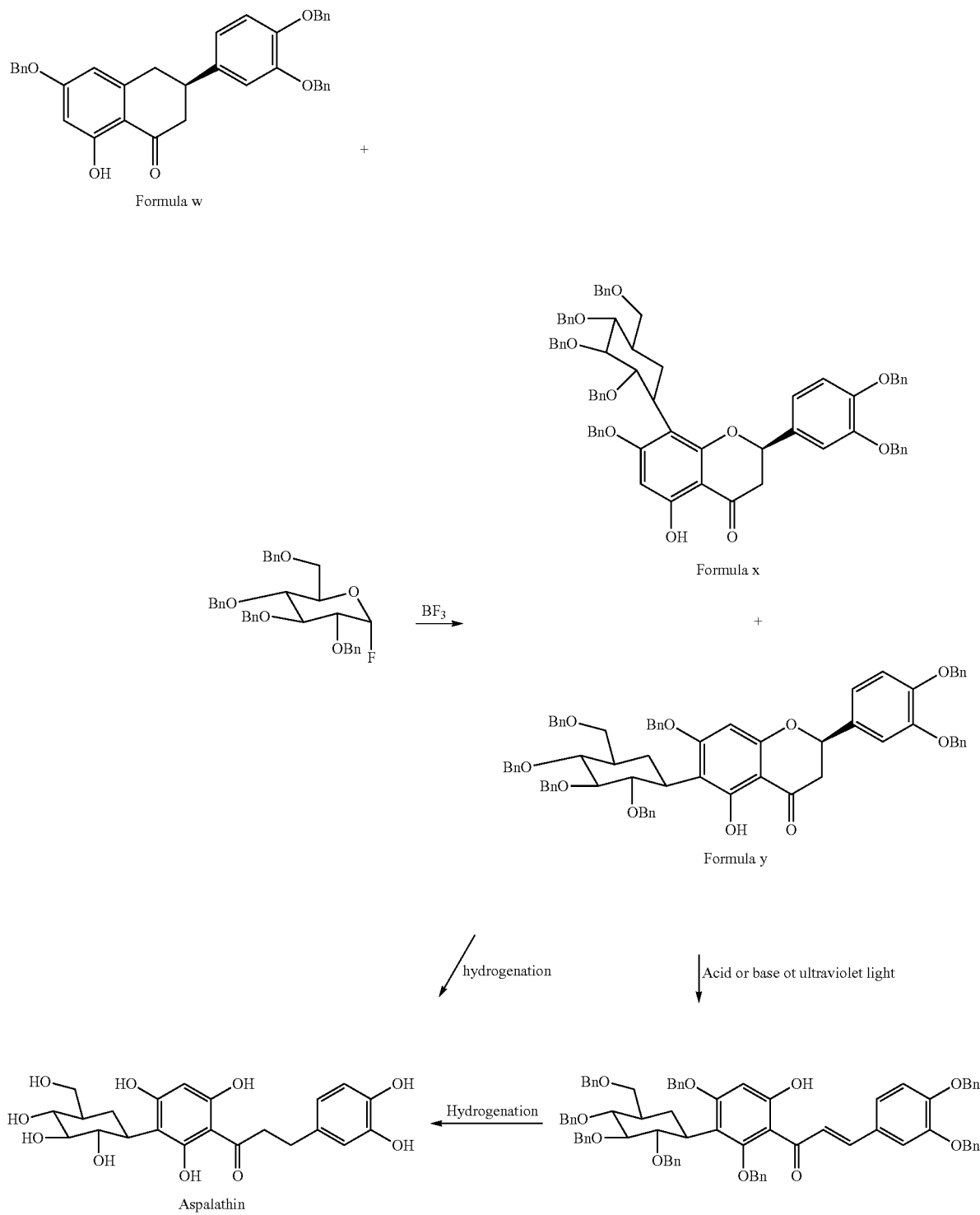

Coupling of a semi protected sugar with one unprotected OH on the aromatic ring gives the desired acetophenone via rearrangement of the O-coupled sugar to a C-coupled sugar according to the method developed by Kumazawa and co-workers (*Bull. Chem. Soc. Jpn.,* 1995, 1379-1384). Importantly, the present invention provides for the coupling of the flavanone (w) with an unprotected OH group on the A-ring to obtain two sugar-flavanone isomers (Formula x and Formula y). Opening of the ring via hydrogenation yields aspalathin (Scheme 9).

In alternative embodiments, the flavanone (w) is coupled to an unprotected sugar to obtain two sugar-flavanone isomers (Formula Z and Formula aa) according to scheme 10. Opening of the ring via hydrogenation yields aspalathin.

Scheme 10.

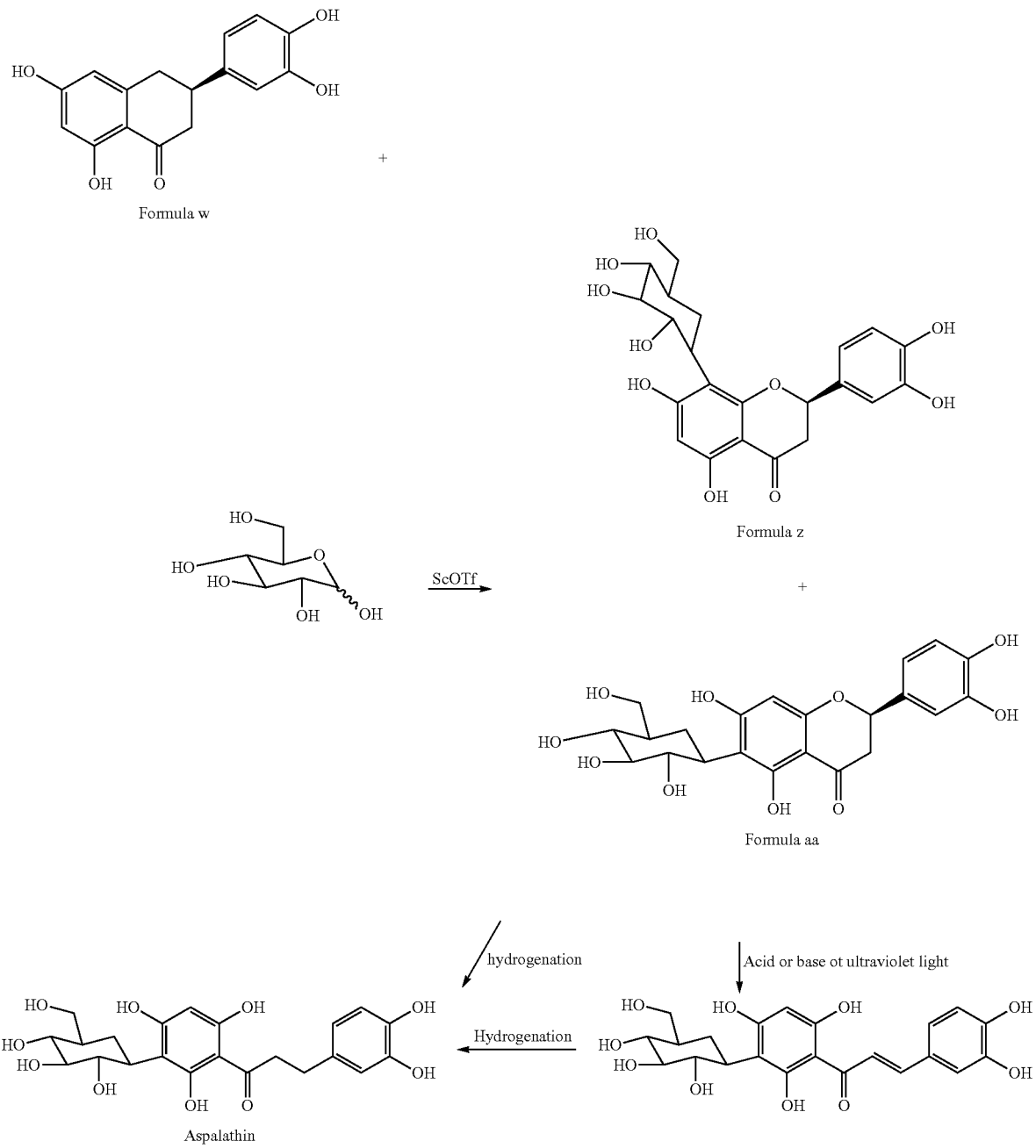

The nucleophilicity of the aromatic ring of a chalcone, dihydrochalcone or flavanone is an important aspect of the invention. It has been found that the nucleophilicity of the aromatic ring can also be enhanced by transforming the carbonyl group of the chalcone, dihydrochalcone and flavanone into an acetal or thioacetal form. The acetal or thioacetal group will also protect the carbonyl group of the chalcone and flavanone upon reduction of the double bond of the chalcone, opening of the heterocyclic ring of the flavanone and removal of the benzyl protecting groups. The acetal is eventually removed by weak acid and water to yield the keto analogues of A. The thioacetal group is eventually removed by methyl iodide in wet methanol or other known methods. A thioacetal is more resistant to Lewis acids than an acetal and harsher conditions can be used to couple the sugar via C-1 to the aromatic ring than with an acetal.

It will be evident to a person skilled in the art that the acetal carbonyl group can be derived from an ethylene glycol, a propane 1,3-diol or linear alcohols. The thioacetal carbonyl protecting group may be derived from 1,2-ethanedithiol, 1,3-propanedithiol or a linear thiol.

In the case of the dihydrochalcone in the perbenzylated form, the acetal prepared with ethylene glycol will have formula ab, the acetal prepared with propane-1,3-diol will have formula ac and the acetal prepared with methanol will have formula ad. The thiacetal prepared with ethylene dithiol will have formula ae, the thioacetal prepared with propane-1,3-dithiol will have formula of and the acetal prepared with methanethiol will have formula ag.

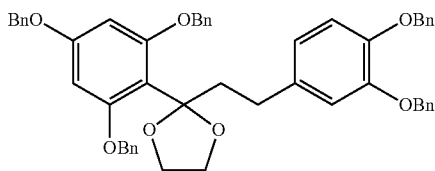

Formula ab

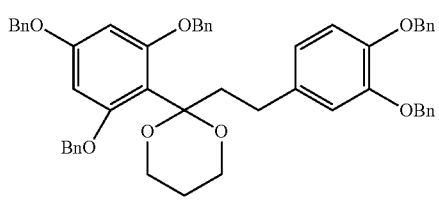

Formula ac

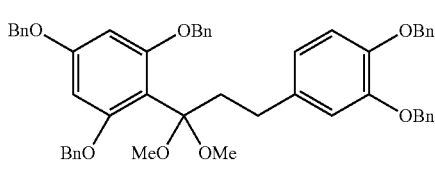

Formula ad

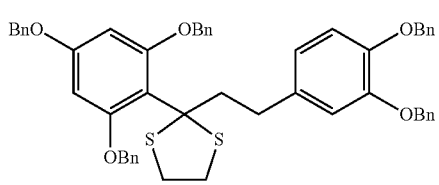

Formula ae

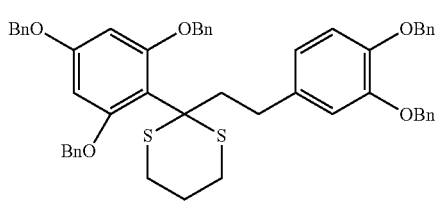

Formula af

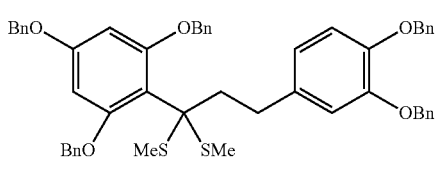

Formula ag

In another embodiment, a perbenzyl 1,2-anhydrosugar equivalent of glucose (Formula f) is used as the C-1 activated sugar molecule (as the glycosyl donor). The 1,2 anhydrosugar is prepared by epoxidation of tri-O-benzyl-D-glycal (g) via known methods. The 1,2 anhydrosugar is then coupled to a perbenzylated nucleophile (e.g Formula ab) with Lewis acid catalysis (e.g. ZnCl$_2$ in THF). Inversion of configuration takes place during coupling to produce an aspalathin analogue (e.g. formula B) with β-configuration on the anomeric C-1 position. Removal of the protecting group on the carbonyl and the benzyl protecting groups yields aspalathin (formula A).

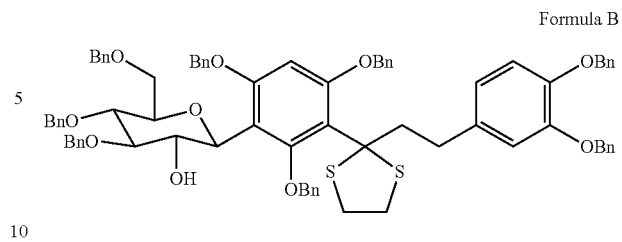

Formula B

The invention will now be described in more detail, by way of example only, with reference to the following non-limiting examples.

EXAMPLES

Example 1

Aspalathin was produced via a chalcone of formula I:

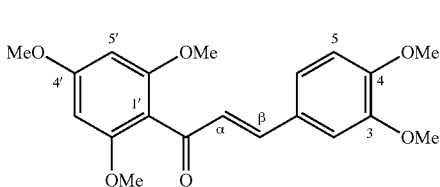

I $\square_H$ (600 MHz, CDCl$_3$, Me$_4$Si) 7.31 (1H, d, H-□), 7.08 (1H, dd, H-6), 7.06 (1H, d, H-2), 6.84 (1H, d, H-5), 6.83 (1H, d, H-□), 6.17 (2H, s, H-3'/H-5'), 3.89 (6H, s, 2× —OCH$_3$), 3.83 (3H, s, —OCH$_3$), 3.75 (6H, s, 2× —OCH$_3$); m/z (ESI) 359 (6, MH$^+$), 347 (100), 217 (33)

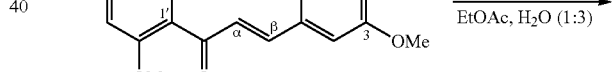

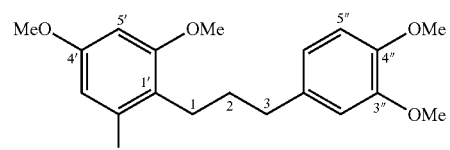

Formula q

To a 6 L pressure bottle was added 20% Pd(OH)$_2$/C (120mg). To this a solution of the methoxy-protected chalcone of formula I (200 mg, 0.034 mol) in EtOAc (HPLC grade, 5 mL) was added, followed by H$_2$O (HPLC grade, 15 mL). The bottle was sealed and purged with H$_2$ at 15 psi (×3). The reactor was pressurized with hydrogen (15 psi) and the reaction mixture was stirred at RT for 12 h. The reaction mixture was extracted with ethyl acetate (3×20mL), filtered through silica gel, the organic layer washed with water and brine, followed by drying over anhydrous MgSO$_4$ The solvent was evaporated under reduced pressure to afford Formula q as a white solid (140 mg, 72%).

$\square_H$ (600 MHz, CDCl$_3$, Me$_4$Si) 6.80 (1H, d, 8.0 Hz, H-5"), 6.76 (2H, m, H-2"/6"), 6.15 (2H, s, H-3'/H-5'), 3.89, 3.87, 3.82, 3.80 (15H, s, 5× —OCH$_3$), 2.62 (4H, m, H-1/3), 1.78 (1H, m, H-2); $\delta_C$ (100.6 MHz, CDCl$_3$) 159.2 (C-4'), 158.9 (C-2'/6'), 148.7 (C-3" or 4"), 146.9 (C-3" or 4"), 135.9 (C-1"), 120.2 (C-2" or 6"), 111.8 (C-5"), 111.5 (C-1'), 111.2 (C-2" or 6"), 90.6 (C-3'/5'), 55.9 (—OCH$_3$), 55.8 (—OCH$_3$), 55.6 (2× —OCH$_3$), 55.3 (—OCH$_3$), 35.5 (C-3), 31.1 (C-2), 22.5 (C-1); m/z (ESI) 347 (15, MH$^+$), 181 (73), 179 (50), 151 (100).

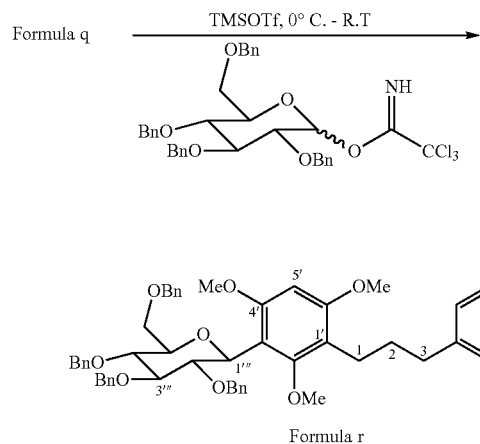

Formula q (50 mg, 0.014 mmol) and (+)-D-glucose imidate [Formula 6] (148 mg, 0.021 mmol) were dissolved in dry DCM (10 mL). Dry 4° A molecular sieves were added and after the reaction mixture was stirred at 0° C. for 10-20 min. the TMSOTf was added dropwise. The reaction was stirred overnight allowing the temperature to rise to room temperature. The reaction mixture was filtered through celite, concentrated under vacuum and chromatographed on a silica gel column (7:3 hexane-EtOAc) to yield Formula r (23%).

$\delta_H$ (600 MHz, DMSO, Me$_4$Si, 140° C.) 7.35-7.20 (15H, m, —OCH$_2$Ph), 7.15-7.05 (3H, m, —OCH$_2$Ph), 6.86 (2H, dd, J=1.7, 7.0 Hz, —OCH$_2$Ph), 6.83 (1H, d, J=8.0 Hz, H-5"), 6.76 (1H, d, J=2.0 Hz, H-2"), 6.68 (1H, dd, J=2.0, 8.0 Hz, H-6"), 6.48 (1H, s, H-5'), 4.85 (1H, d, J=12.0 Hz, —O—CH$_2$Ph), 4.81 (2×1H, d, J=12.0 Hz, 2× —O—CH$_2$Ph), 4.72 (1H, d, J=9.3 Hz, H-1'''), 4.66 (1H, d, J=11.7 Hz, —O—CH$_2$Ph), 4.53 (1H, d, J=12.0 Hz, —O—CH$_2$Ph), 4.47 (1H, d, J=12.4 Hz, —O—CH$_2$Ph), 4.42 (1H, d, J=11.4 Hz, —O—CH$_2$Ph), 4.37(1H, t, J=9.3 Hz, H-2"'), 4.00 (1H, d, J=11.4 Hz, —O—CH$_2$Ph), 3.83, 3.78, 3.75, 3.74, 3.68 (5×3H, s, —OCH$_3$), 3.73-3.55 (5× H, sugar protons) 2.65-2.55 (4H, m, H-1/H-3), 1.85-1.75 (2H, m, H-2); $\delta_C$ (100.6 MHz, DMSO, Me$_4$Si, 140° C.) 159.8 (C-2'/6'), 159.0 (C-4'), 150.2 (C-4"), 148.4 (C-3"), 139.7, 139.3, 136.2 (C-1"), 128.4-127.4 (C-Bn), 121.2 (C-6"), 114.9 (C-2"), 114.6 (C-5"), 95.4 (C-5'), 87.3 (C-sugar), 80.6 (C-2'''), 79.5 (C-sugar), 79.4 (C-sugar), 74.6 (—OCH$_2$Ph), 74.2 (—OCH$_2$Ph), 74.1 (C-1'''), 73.6 (—OCH$_2$Ph), 73.2 (—OCH$_2$Ph), 70.5 (C-sugar), 62.7 (C-sugar), 57.2, 57.1, 56.9, 56.5, 56.3 (5× —OCH$_3$), 35.4 (C-3), 31.1 (C-2), 23.4 (C-1)

Oxidation of the compound of Formula r (IBX), followed by deprotection yielded aspalathin.

Example 2

Aspalathin was produced via a dihydrochalcone of formula II

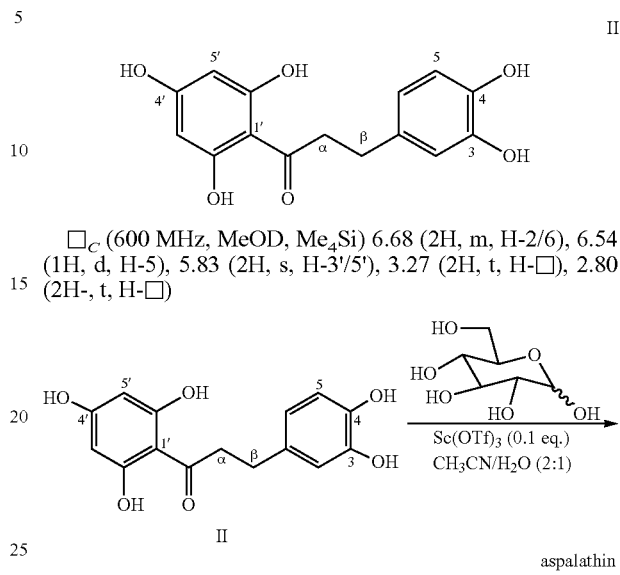

$\delta_C$ (600 MHz, MeOD, Me$_4$Si) 6.68 (2H, m, H-2/6), 6.54 (1H, d, H-5), 5.83 (2H, s, H-3'/5'), 3.27 (2H, t, H-□), 2.80 (2H-, t, H-□)

A mixture of D-glucose (643 mg, 3.57 mmol), dihydrochalcone of formula II (300 mg, 1.08 mmol), and a catalytic amount of Sc(OTf)$_3$ (58.6 mg, 0.119 mmol, 0.03 equivalent) in CH$_3$CN [(6 mL)/H$_2$O (3 mL)] was refluxed for about 10 hr. The reaction mixture was filtered through a silica gel pad, the filtrate concentrated under reduced pressure and purified by gradient column silica gel chromatography using hexane (100%), followed by, hexane/acetone 9:1; 8:2; 7:3; 6:4; 5.5: 4.5; 5:5 to obtain aspalathin (109 mg, 59%).

NMR data corresponded to published data:
Yepremyan, A, Salehani, B; Minehan, T. G. *Org. Lett.*, 2010, 12 (7), pp 1580-1583
1H NMR Aspalathin
1H NMR: (400 MHz, CDCl3)
6.63 (d, J=7.6 Hz, 1H); 6.61 (s, 1H); 6.47 (d, J=8.0 Hz, 1H); 5.93 (s, 1H); 4.54 (d, J=9.6 Hz, 1H); 3.87 (t, J=8.4 Hz, 1H); 3.66 (d, J=11.2 Hz, 1H); 3.42 (d, J=8.8 Hz, 1H); 3.21 (t, J=7.6 Hz, 2H); 3.14 (m, 3H) 2.70 (t, J=7.6 Hz, 2H).
13C NMR: (100 MHz, CDCl3) 204.9; 165.5; 164.4; 162.2; 145.5; 143.8; 133.0; 119.3; 116.2; 115.9; 104.4; 104.1; 95.0; 81.7; 79.4; 74.1; 70.8; 70.5; 61.7; 45.8; 30.2

Example 3

An intermediate III for use in the production of aspalathin was produced as follows.

4,6-Bis-hydroxy-3-C-(2,3,4,6-tetra-O-benzyl-β-D-glucopyranosyl)-2-hydroxyacetophenone III

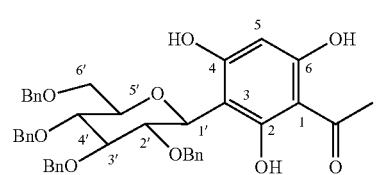

To a solution of 2,3,4,6-tetra-O-benzyl-glycosyl imidate [Formula 6] (2.32 g, 3.4 mmol) in DCM (25 mL) and 2,4,6-trihydroxy-acetophenone (1.6 g, 10 mmol) in THF (3 mL), was added 0.1 mL (1.2 mmol) of BF₃OEt₂, followed by stirring at −78° C. for 2 h. The reaction mixture was warmed up to ambient temperature for 2 h, and then refluxed at 55° C. for 5 h, after which aqueous NaHCO₃ (5 mL) was added the reaction mixture was stirred vigorously for 5 min. The resulting mixture was filtered through a short flash celite® column, dried over MgSO₄ and then evaporated in vacuo. The residue was purified by flash-column chromatography on silica gel (4:1:1 hexane-EtOAc) to give compound III (1.49 g, 48%) as a colourless syrup.

Although NMR data was has yet to be obtained for this intermediate, its production is evidenced by the NMR data for compound IV. The product III was acetylated to yield IV to facilitate structure elucidation:

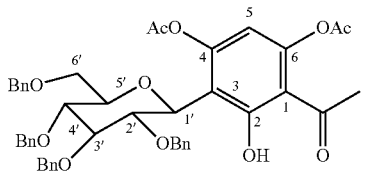 [SMILES: CC(=O)Oc1cc(OC(C)=O)c(C2OC(COCc3ccccc3)C(OCc3ccccc3)C(OCc3ccccc3)C2OCc2ccccc2)c(O)c1C(C)=O]

IV

NMR table for compound IV

1HNMR(CDCl₃)
δ = 14.62 ppm (1 × H, s, OH)
δ = 7.50-7.12 ppm
(20 × H, aromatic from 6 × OBn)
δ = 6.18 ppm (1 × H, s, H5)
δ = 5.2-4.2 ppm
(12 × H, benzylic from 6 × OBn)
δ = 4.85
(1 × H, d, J = 9.5 Hz, H1'/anomeric)
δ = 4.21 ppm (1 × H, triplet,
J = 9.4 Hz, H2')
δ = 3.72 (2 × H, m, H6')
δ = 3.65 (1 × H, m, H3')
δ = 3.58 (1 × H, m, H4')
δ = 3.47 (1 × H, m, H5')
δ = 2.55 (3 × H, m, acetyl)
δ = 2.35 (3 × H, m, O-acetyl)
δ = 2.07 (3 × H, m, O-acetyl)

The compound of formula III can be coupled with benzaldehyde to form a protected chalcone, which can be hydrogenated and deprotected to yield aspalathin.

The invention claimed is:

1. A method for synthesising aspalathin having the Formula A:

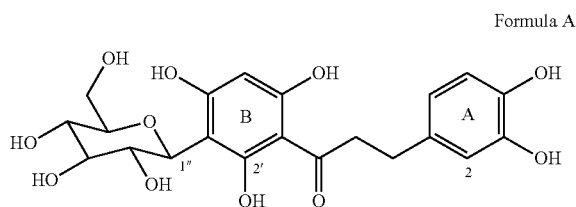

Formula A wherein the method comprises the step of coupling an unprotected or protected sugar to an unprotected or protected dihydrochalcone or chalcone, or coupling the sugar to an intermediate for producing a dihydrochalcone or chalcone followed by coupling of the sugar-intermediate adduct to a further intermediate for producing a dihydrochalcone or chalcone and transforming the product thereof into a compound of formula A.

2. A method according to claim 1, wherein a protected sugar is coupled to a dihydrochalcone, the nucleophilicity of the dihydrochalcone towards the anomeric (C-1) carbon of the being activated by removing the carbonyl from the dihydrochalcone, which carbonyl is reintroduced after coupling.

3. A method according to claim 1, wherein the electrophilicity at the anomeric (C-1) carbon of the sugar is activated by substituting a hydroxy group at C-1 of the sugar with a substituent selected from trichloroacetimidate, trifluoroacetimidate, acetate, trifluoroacetate, a halide, and a sulfur- or selenium containing leaving group.

4. A method according to claim 1, wherein a chalcone is formed from the coupling of a sugar to an acetophenone having one free OH on the aromatic A-ring thereof, the unprotected OH reacting to form an O-glycoside, which O-glycoside either rearranges spontaneously to the C-glycoside or is transformed to the desired C-glycoside, the resultant chalcone being selectively reduced to a compound of formula A.

5. A method according to claim 1, wherein a fluorinated sugar is coupled to a flavone or flavanone with a free phenolic OH on the aromatic ring thereof, the coupled product being transformed via a chalcone to a compound of formula A.

* * * * *